United States Patent [19]

Vogel et al.

[11] 4,312,834

[45] Jan. 26, 1982

[54] DIAGNOSTIC AGENT FOR THE DETECTION OF COMPONENT MATERIALS IN LIQUID AND PROCESS FOR PRODUCING SAME

[75] Inventors: Peter Vogel, Weinheim; Hans-Peter Braun, Hemsbach; Dieter Berger, Viernheim; Wolfgang Werner, Mannheim, all of Fed. Rep. of Germany

[73] Assignee: Boehringer Mannheim GmbH, Mannheim, Fed. Rep. of Germany

[21] Appl. No.: 125,382

[22] Filed: Feb. 28, 1980

[30] Foreign Application Priority Data

Mar. 15, 1979 [DE] Fed. Rep. of Germany ....... 2910134

[51] Int. Cl.$^3$ ............... G01N 33/52; G01N 33/72; G01N 33/92
[52] U.S. Cl. .................... 422/56; 23/230 B; 23/913; 23/931; 23/932; 252/408; 435/4; 435/11; 435/805; 427/393.5

[58] Field of Search ............... 23/230 B, 931, 913, 23/932; 422/56–58; 428/325, 328, 333, 342; 435/805, 4, 11; 252/408

[56] References Cited

U.S. PATENT DOCUMENTS

| | | | |
|---|---|---|---|
| 3,100,722 | 8/1963 | Herrmann et al. | 428/325 |
| 3,108,009 | 10/1963 | Clancy et al. | 428/325 X |
| 3,630,957 | 12/1971 | Rey et al. | 422/56 X |
| 3,992,158 | 11/1976 | Przybylowicz et al. | 435/28 X |
| 4,250,256 | 2/1981 | Wielinger et al. | 435/805 X |

FOREIGN PATENT DOCUMENTS 1240884 7/1971 United Kingdom ............... 252/408

Primary Examiner—Arnold Turk
Attorney, Agent, or Firm—Sprung, Felfe, Horn, Lynch & Kramer

[57] ABSTRACT

Diagnostic agent for the detection of component materials, in liquids and method of production. The diagnostic agent includes a water resistant film composed of a film-former and contains a film opener in the form of fine, insoluble inorganic or organic particles.

9 Claims, No Drawings

DIAGNOSTIC AGENT FOR THE DETECTION OF COMPONENT MATERIALS IN LIQUID AND PROCESS FOR PRODUCING SAME

The present invention is concerned with a diagnostic agent for the detection of components in liquids.

The detection of component materials of liquids by means of test strips is of ever increasing importance. In many cases, they provide a simple, economical and rapid detection process. Test strips are widely used in urine diagnosis for qualitative and semiquantitative detection processes. Special test strips can also be used for the detection of component materials of blood and serum in medical diagnosis. Furthermore, test strips are widely used for investigating drinks, drinking water, waste water and other liquids occurring in industry.

One difficulty for the quantitative evaluation of the detection methods, especially for high molecular weight and corpuscular components of liquids, on the basis of test strips has hitherto been the fact that paper has been used almost exclusively as absorbent carrier. By way of example, mention may be made of Tallqvist's method of determination of haemoglobin. The homogeneity with regard to layer thickness, structure and composition, which is necessary for quantitative tests, is difficult to achieve in the case of papers. Furthermore, when using papers for quantitative tests, it has proved to be disadvantageous that an exact measurement of the sample material is frequently necessary.

A great advance in the quantitative determination of low molecular weight materials was provided by the use of films according to Federal Republic of Germany Patent Specification No. 1,598,153. The properties of these films can be adapted to the particular analytical process. They do not require a precise measurement of the material to be investigated and react uniformly with urine, plasma, serum and whole blood. After a short reaction period, excess sample material is simply wiped off. Because of the small pore size of these films, they permit a separation of dispersed or suspended components in the solution to be investigated, for example of erythrocytes in blood, from low molecular weight, dissolved component materials.

For the improvement of their properties, these films can also contain small amounts of adjuvants, for example chalk or titanium dioxide, for increasing the remission.

However, these films cannot be used when cellular components or large molecules, for example enzymes, are to be determined. Such substances do not penetrate or do not penetrate sufficiently into the film in order to bring about a measurable reaction. For this reason, with this film principle, it is not possible to produce tests which can be used, for example, for the detection of haemoglobin, cholesterol in lipoproteins or enzymes.

Surprisingly, it has now been found that absorbent, "open" films are obtained when solid materials in the form of fine, insoluble organic or inorganic particles are added to aqueous dispersions or organic solutions of film-forming substances from which water-insoluble films are to be formed.

Thus, according to the present invention, there is provided a diagnostic agent for the detection of component materials in liquids, comprising a water-resistant film containing a film opener in the form of fine, insoluble inorganic or organic particles and the reagents necessary for the detection.

Since the solid material does not itself "react", its composition is not critical and use can be made, for example, of cellulose, kieselguhr, silica gel, precipitated gypsum, calcium carbonate, kaolin, a polyamide, glass or the like.

The ratio of this solid material, which is herein called a "film opener", to the film former can be 20:1 to 0.5:1 and preferably 5:1 to 1:1. The ratio depends upon the nature of the film opener and the film former used, as well as upon the intended use. With increasing amounts of film opener and increasing specific surface area of the material employed, the film becomes more absorbent.

When the diagnostic agent according to the present invention is to be used for the detection of high molecular weight and corpuscular materials, the ratio of film opener to film former is preferably 1:1 to 20:1 and more preferably 2:1 to 5:1 and when it is to be used for the detection of low to medium molecular weight substances, the ratio of film opener to film former is preferably 0.5:1 to 2:1.

If the proportion of film opener exceeds a certain limit, then the film becomes mechanically unstable. If too little film opener is added to the film, then it is impermeable to high molecular weight and cellular components. Thus, for example, the ratio of film opener to film former is preferably 5:1 to 2:1 when polyamide or precipitated gypsum is used as film opener and an aqueous dispersion of polyvinyl propionate is used as film former. If, on the other hand, kieselguhr is used, then the ratio should preferably be 2:1 to 1:1.

Preferred film formers include organic synthetic resins, such as polyvinyl esters, polyvinyl acetals, polyacrylic esters, polymethacrylic acid, polyacrylamides, polyamides, polystyrene and co-polymers of, for example, butadiene and styrene and of maleic acid esters and vinyl acetate. However, other film-forming, natural and synthetic organic polymers, as well as mixtures thereof, can be used, preferably in the form of aqueous dispersions. However, the film formers can also be dissolved in organic solvents, for example a co-polymer of vinyl chloride and vinyl propionate can be dissolved in ethyl acetate.

The dispersions or solutions can be coated on a substrate to give a uniform layer which, after drying, gives a water-resistant film.

A special advantage of the diagnostic agents according to the present invention in comparison with absorbent papers is that the films can be produced more simply, more uniformly and reproducably. The film can be used with the substrate as a carrier or, for carrying out the detection reaction, can be pulled off the substrate and/or applied to another carrier. Carriers for the coated films are preferably synthetic resin films. However, other films and foils, papers, synthetic resin plates, glass, metal and the like can also be used as carriers if it is appropriate for the purpose of use.

The present invention also provides a process for the production of a diagnostic agent, wherein a solution or dispersion of a film former in an appropriate liquid is mixed with a film opener and optionally with the necessary reagents and adjuvants, the mixture is applied to a substrate to give a thin film and the liquid is evaporated, whereafter the resultant film is, if necessary, impregnated with reagents and adjuvants.

The reagents necessary for the detection reaction are normally added directly to the dispersion. Insofar as it is advantageous to do so, the formed film can, however, also be impregnated with them. A preimpregnation of the film opener with the reagents is also possible. The processes can also be combined in such a manner that, for example, certain components are added to the dispersion and the others are subsequently impregnated into the film. In this way, a certain spatial separation of the components is achieved, which can result in more stable or more reactive tests. A further possibility of separating formulation components from one another is to distribute them among various coating masses which are then coated on in the optimum sequence one after the other so that a multi-layer system is obtained.

If necessary, thickening agents, emulsifiers, dispersion agents, pigments, for example titanium dioxide, plasticisers, wetting agents and the like can also be added.

Dispersion agents, emulsifiers and thickening agents serve for the production and stabilization of the dispersions. Pigments, for example titanium dioxide, which can also function as film openers, improve the remission properties of the films by providing for the smallest possible transparency and an increased remission of the films. This is of particular advantage when test agents so obtained are to be evaluated by remission photometry. The use of plasticizers makes it possible to obtain film coating masses, as well as films, with optimum properties. Thus, for example, their stability, their viscosity, their adhesion to the substrate to be coated and the like can be improved. Wetting agents are used in order to achieve a better wetting of the film by the sample material. At the same time, they can catalyze reactions or stabilize formulations or make the reaction colors more brilliant and with greater contrast.

Although the above-described films were preferably developed for the detection of high molecular weight and corpuscular components, they can, of course, also be used for the detection and determination of low molecular weight compounds. In comparison with the films according to Federal Republic of Germany Patent Specification No. 1,598,153, they have the advantage of sucking up the solution to be investigated more strongly and quickly and thereby of showing more intensive reactions. With appropriate choice of the ratio of film opener to film former, which, in addition, also depends upon the nature of these materials. for example of 0.5:1 to 2:1, it is, in some cases, possible to suppress the penetration of high molecular weight materials into the film, which otherwise could give rise to disturbances, and only to detect or determine low molecular weight materials. The diagnostic agents according to the present invention are preferably employed for the detection of component materials in body fluids, for example urine, blood, serum and saliva. However, in suitably modified form, they can also be used in other aqueous media, for example, drinking water, waste water and the like, and possibly also in organic solvents in which they are insoluble.

A great advantage of the diagnostic agents according to the present invention, which contain the required reagents, is that they can be readily adapted to the intended purpose of use by selection of the most appropriate film formers, film openers and the like. A further great advantage is that a precise measurement of the sample can be omitted because the film itself measures the sample material, excess sample being simply wiped off after a definite reaction time.

The following Examples are given for the purpose of illustrating the present invention:

EXAMPLE 1

For the production of a reagent film for the detection of cholesterol in serum, a dispersion was prepared with the following composition:

| | |
|---|---|
| cellulose | 5 g. |
| polyvinyl propionate dispersion (50% in water) | 3 g. |
| methylhydroxypropyl-cellulose | 0.042 g. |
| titanium dioxide powder | 2 g. |
| cholesterol esterase | 1200 U |
| cholesterol oxidase | 800 U |
| peroxidase | 26,000 U |
| gallic acid | 0.0032 g. |
| a solution of 0.2 g. 3,3',5,5'-tetramethylbenzidine and 0.17 g. dioctyl sodium sulphosuccinate in 0.74 ml. acetone | 1 ml. |
| potassium dihydrogen phosphate | 0.049 g. |
| disodium hydrogen phosphate dihydrate | 0.167 g. |
| distilled water | 19.5 ml. |

The mixture was applied to a polycarbonate film in a 300$\mu$ thick layer and subsequently dried with warm air. The reagent layer thus obtained gave, with cholesterol-containing sera, well graduated, blue colorations dependent upon the concentration of cholesterol.

After adjustment of a remission photometer ("Reflomat") provided with a linear scale with an unused test strip to the 0 scale reading and with a black foil to the 100 scale reading, for the blue colorations corresponding to the cholesterol concentrations, there were obtained the following measurement values:

| | |
|---|---|
| 0 mg. | 0 scale reading |
| 100 mg. | 6 scale reading |
| 200 mg. | 44 scale reading |
| 300 mg. | 66 scale reading |
| 400 mg. | 76 scale reading |
| 500 mg. | 83 scale reading |
| 600 mg. | 88 scale reading |
| black control film | 100 scale reading |

EXAMPLE 2

For a test for the detection of erythrocytes in urine, there was first prepared a film from the following mixture:

| | |
|---|---|
| polyvinyl propionate dispersion (50% in water) | 50 g. |
| kaolin | 60 g. |
| dioctyl sodium sulphosuccinate | 2 g. |
| distilled water | 140 ml. |

The mixture was applied in a 400$\mu$ thick layer on to a polycarbonate film and subsequently dried with warm air. The film so obtained was impregnated with the following Solutions I and II and, after each impregnation, dried with warm air.

| Solution I | |
|---|---|
| ethylenediamine-tetraacetic acid disodium salt | 1 g. |
| trisodium citrate dihydrate | 15.7 g. |
| citric acid monohydrate | 3.48 g. |
| phosphoric acid trimorpholide | 30.5 g. |
| benzolight yellow (C.I. direct yellow | 0.048 g. |

| Solution I | |
|---|---|
| No. 12) | |
| distilled water | 190 ml. |

3.2 g. 2,5-Dimethyl-2,5-dihydroperoxyhexane, dissolved in 60 ml. methanol, were added thereto.

| Solution II | |
|---|---|
| 3,3'5,5'-tetramethylbenzidine | 0.56 g. |
| dioctyl sodium sulphosuccinate | 1.0 g. |
| phenanthridine | 1.4 g. |
| phenyl semicarbazide | 0.06 g. |
| toluene | 100 ml. |
| methoxyethanol | 10 ml. |
| petroleum ether | 90 ml. |

The film thus obtained gave green colorations with erythrocyte-containing urines.

EXAMPLE 3

A film for the detection of nitrite in urine was obtained in the following manner:

Into the Solution (a) described below were stirred 10 g. cellulose, followed by filtering off and drying in warm air:

| Solution (a) | |
|---|---|
| 3-hydroxy-1,2,3,4-tetrahydro-benzo-[h]-quinoline | 0.392 g. |
| sulphanilamide | 0.344 g. |
| L-tartaric acid | 5.00 g. |
| methanol | ad 200 ml. |

With the cellulose impregnated in this manner, there was produced the following coating mass:

| impregnated cellulose | 10.00 g. |
|---|---|
| methylhydroxypropyl cellulose | 0.09 g. |
| polyvinyl propionate dispersion (50% in water) | 5 g. |
| 10% solution of dioctyl sodium sulphosuccinate in acetone | 3 ml. |
| distilled water | 35 ml. |

A 400μ thick layer of the mass was applied to a polyester film and dried with warm air. The water-insoluble film gave red color reactions with nitrite-containing liquids, for example urine and industrial waste water.

EXAMPLE 4

For the detection of haemoglobin in blood, a reagent film was produced from the following mixture:

| cellulose | 20 g. |
|---|---|
| polyvinyl propionate dispersion (50% in water) | 15 g. |
| dioctyl sodium sulphosuccinate | 0.3 g. |
| 0.5 mole phosphate buffer (pH 7) | 75 ml. |

The mixture was applied in a 200μ thick layer to a polyester film and dried with warm air.

When, from a series of dilutions of blood with varying haemoglobin content, 1 drop of each dilution was allowed to react for 1 minute on the test film, then, after wiping off the drop with wadding, graduated colorations were obtained.

When the resultant colorations of the test strips were measured with a remission photometer (Zeiss PMQ 3) at 540 nm, then, in dependence upon the haemoglobin concentration, the following measurement values were obtained:

| g. haemoglobin/liter | % remission |
|---|---|
| 53 | 46.1 |
| 100 | 38.8 |
| 150 | 31.7 |
| 201 | 25.5 |

EXAMPLE 5

For the ascertainment of the limits of the process, the mixture of film opener and film former were, analogously to Example 4, varied and films obtained with the following properties:

| film opener/film former | properties in the case of reaction with erythrocytes in blood |
|---|---|
| kieselguhr:polyvinyl propionate | |
| 0.5:1 | stable film, erythrocytes only penetrate at a few places |
| 1:1 | stable film, uniform reaction of the whole film |
| 4:1 | uniform reaction of the whole film; film material is partly removed by wiping off |
| gypsum:polyvinyl propionate | |
| 3:1 | stable film, slightly colored |
| 4 to 10:1 | stable film, uniformly deep coloration |
| 20:1 | In the case of slight pressure, wipe-resistant film, uniform coloration, drops "chromatograph" on the edge |

It will be understood that the specification and examples are illustrative, but not limitative of the present invention and that other embodiments within the spirit and scope of the invention will suggest themselves to those skilled in the art.

What is claimed is:

1. Diagnostic agent for the detection of component materials in liquids, comprising a water resistant film comprising a film-former and containing a film opener in the form of fine, insoluble inorganic or organic particles, and the reagents for said detection, wherein the ratio of film opener to film former is 20:1 to 0.5:1 by weight.

2. Diagnostic agent as claimed in claim 1 wherein the ratio of film opener to film former is 5:1 to 1:1 by weight.

3. Diagnostic agent as claimed in claim 1 for the detection of materials with a low to medium molecular weight, wherein the ratio of film opener to film former is 0.5:1 to 2:1 by weight.

4. Diagnostic agent as claimed in claim 1 wherein said water resistant film is fixed to a carrier.

5. Diagnostic agent as claimed in claim 1 for the detection of high molecular weight and corpuscular materials, wherein the ratio of film opener to film former is 1:1 to 20:1 by weight.

6. Diagnostic agent as claimed in claim 5 wherein the ratio of film opener to film former is 2:1 to 5:1 by weight.

7. Process for the production of a diagnostic agent for the detection of component materials in liquids, the diagnostic agent having a water resistant film composed of a film-former and containing a film opener in the form of fine, insoluble inorganic or organic particles, and the reagents for said detection, which process comprises mixing the reagents for said detection, and optionally adjuvants, with a solution or dispersion of a film former in liquid medium and the film opener, the film former and film opener being added in an amount to result in a ratio of film opener to film former of 20:1 to 0.5:1 by weight, applying said mixture to a substrate to form a thin film thereon, and evaporating the liquid therefrom to result in an impregnated substrate.

8. Process as claimed in claim 7 wherein said film is removed from said substrate and is fixed to a carrier.

9. Process for the production of a diagnostic agent for the detection of component materials in liquids, the diagnostic agent having a water resistant film composed of a film-former and containing a film opener in the form of fine, insoluble inorganic or organic particles, and the reagents for said detection, which process comprises mixing a solution or dispersion of a film former in liquid medium with a film opener in an amount to form a ratio of film opener to film former of 20:1 to 0.5:1 by weight, applying said mixture to a substrate to form a thin film thereon, evaporating the liquid from said film, and thereafter applying to said film the reagents for said detection and optionally adjuvants, to result in an impregnated substrate.

* * * * *